(12) United States Patent
Nunes

(10) Patent No.: US 11,636,948 B2
(45) Date of Patent: Apr. 25, 2023

(54) INSTRUMENT KIT TRACKING SYSTEM

(71) Applicant: Q Med Innovations, Inc., Middletown, RI (US)

(72) Inventor: Victor M. Nunes, Middletown, RI (US)

(73) Assignee: Q Med Innovations, Inc., Middletown, RI (US)

( * ) Notice: Subject to any disclaimer, the term of this patent is extended or adjusted under 35 U.S.C. 154(b) by 426 days.

(21) Appl. No.: 15/930,969

(22) Filed: May 13, 2020

(65) Prior Publication Data

US 2020/0373008 A1    Nov. 26, 2020

Related U.S. Application Data

(60) Provisional application No. 62/850,904, filed on May 21, 2019.

(51) Int. Cl.
| | | |
|---|---|---|
| *G16H 40/40* | (2018.01) |
| *A61B 50/30* | (2016.01) |
| *G16H 40/67* | (2018.01) |
| *G16H 40/20* | (2018.01) |
| *H04W 4/029* | (2018.01) |
| *A61L 2/07* | (2006.01) |
| *G01K 3/00* | (2006.01) |
| *G01K 13/00* | (2021.01) |
| *G01S 19/42* | (2010.01) |
| *G06Q 50/28* | (2012.01) |

(52) U.S. Cl.
CPC ............. *G16H 40/40* (2018.01); *A61B 50/30* (2016.02); *A61L 2/07* (2013.01); *G01K 3/005* (2013.01); *G01K 13/00* (2013.01); *G01S 19/42* (2013.01); *G06Q 50/28* (2013.01); *G16H 40/20* (2018.01); *G16H 40/67* (2018.01); *H04W 4/029* (2018.02); *A61L 2202/24* (2013.01)

(58) Field of Classification Search
CPC ........ G16H 40/40; G16H 40/67; G16H 40/20; A61B 50/30; H04W 4/029; A61L 2/07; G01K 3/005; G01K 13/00; G01S 19/42; G06Q 50/28
USPC ............................................................ 705/2
See application file for complete search history.

(56) References Cited

U.S. PATENT DOCUMENTS

| | | |
|---|---|---|
| 7,518,502 B2 | 4/2009 | Austin et al. |
| 7,701,334 B1 | 4/2010 | Perkins et al. |
| 2009/0109033 A1 | 4/2009 | Salvat |
| 2010/0155098 A1 | 6/2010 | Sun et al. |

(Continued)

*Primary Examiner* — Kerri L McNally
(74) *Attorney, Agent, or Firm* — David R. Josephs; Hinckley, Allen & Snyder LLP

(57) ABSTRACT

The present disclosure is directed to an instrument kit tracking system that includes a housing that has tracking electronics that is contained in either a compartment or wall of the medical instrument kit or in a standalone unit that is affixed to a medical instrument kit to contain and protect an electronic device from external temperatures between 120-135° C.; where the medical instrument kit contains at least one medical instrument. The internal temperature of the instrument kit tracking system is maintained such that the electronic device contained therein is operable when the external temperature is between 120-135° C. A further layer, such as of a thickness of 1 mm, resides between the electronic device and the outer walls of the compartment or module. Access to the tracking electronics may also be selectively lockable.

13 Claims, 5 Drawing Sheets

(56) References Cited

U.S. PATENT DOCUMENTS

| | | | |
|---|---|---|---|
| 2017/0224454 A1* | 8/2017 | Oien | A61C 19/002 |
| 2017/0224859 A1 | 8/2017 | Broninx et al. | |
| 2017/0308188 A1* | 10/2017 | Hayashi | G06F 3/03543 |
| 2017/0348452 A1 | 12/2017 | Kuzelka | |
| 2017/0365495 A1 | 12/2017 | Sun et al. | |
| 2018/0285605 A1* | 10/2018 | White | G06K 7/10316 |
| 2019/0000586 A1 | 1/2019 | Singh et al. | |
| 2019/0321132 A1* | 10/2019 | Weir | A61B 50/33 |
| 2020/0261183 A1* | 8/2020 | Beck | H01L 41/042 |

\* cited by examiner

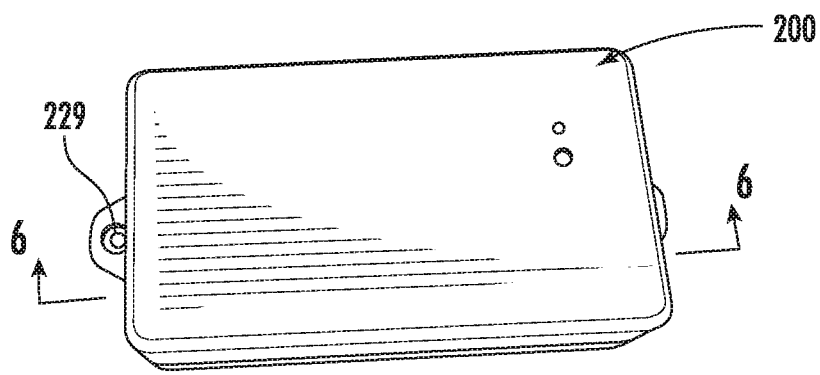
FIG. 5
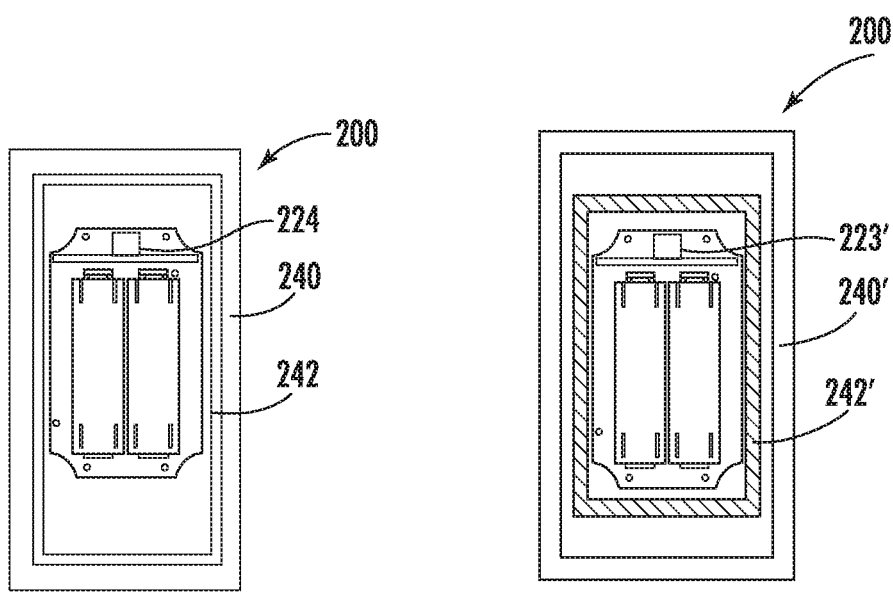
FIG. 6
FIG. 7

INSTRUMENT KIT TRACKING SYSTEM

CROSS REFERENCE TO RELATED APPLICATIONS

This application claims benefit of U.S. Provisional Patent Application No. 62/850,904, filed May 21, 2019, the entire contents thereof are incorporated by reference.

BACKGROUND OF THE INVENTION

The present disclosure generally relates to the medical industry, specifically to medical instrument kits as well as the object tracking industry, including tracking systems for medical instrument kits.

In the medical industry, current instrument kits suffer from the inability to properly track such instrument kits once they are deployed to the sales force network or hospitals. These instrument kits are often assets of the original equipment manufacturers (OEM) and often placed on loan to a hospital to support a surgical procedure. One issue with such kits is, once they are out of the OEM's control, the sets are often misplaced, lost, or simply contained within the sales network without further visibility by the OEM. These lost, misplaced, or otherwise disposed kits come at an extreme cost to the OEM's each year.

Additionally, there is a concern in the industry and by the FDA as to how instruments are being managed. Such management can include the calibration, repair, or ultimately replacement of the instruments once they are deployed to support surgery. Current instrument kits fail to provide a way of tracking whether a kit has been in one or a hundred surgeries. As such, the prior art systems fail to provide the OEM, hospitals, or other users the current lifecycle of the kits or the instruments contained therein.

SUMMARY OF THE INVENTION

Thus, the instrument kit tracking system and methods of the present invention can provide the ability to monitor and report on a daily basis the exact location of each kit without human interaction. Moreover, the instrument kit tracking system and method of the present invention can record and transmit, within the same daily schedule, all date stamps, locations, and number of surgeries the kit has been involved in. A cloud-based system can be included to capture data on a daily basis and report out to the user or manager the particular status of each deployed kit. The cloud-based system can additionally alert end users of any kit that may have reached a predefined limitation on the number of surgeries performed so that the kit can be returned and instruments replaced or calibrated before going back out for deployment. The instrument kit tracking system and method of the present invention offers greater efficiency in inventory management, deployment, accountability of the assets, automatic annual inventory auditing, complete compliance to instrument usage and documentation, and ease of inventory recovery during product recalls.

There have been attempts in the prior art to address the foregoing known problems in the industry. For example, there have been attempts to track surgical assets with software applications and phone apps to facilitate the management of the location of these sets and replenishment of implant or instrument inventory. These efforts are inadequate and suffer from inaccuracy and lack of integrity because these tools require manual input and many times data is corrupted due to the lack of input given to the systems on a timely basis.

For the foregoing reasons, there is a need for a system and method for continuous tracking of surgical, or medical kits, that can continuously track even during multiple high temperature sterilization processes.

BRIEF DESCRIPTION OF THE DRAWING FIGURES

The novel features that are characteristic of the present disclosure are set forth in the appended claims. However, the disclosure's preferred embodiments, together with further objects and attendant advantages, will be best understood by reference to the following detailed description taken in connection with the accompanying drawings in which:

FIG. 5 is a second embodiment of the present invention where the location tracking electronics is contained within a separate electronics module that is secured to an instrument kit, such as by rivets, or the like;

FIG. 6 is a close-up cross-sectional view through line 6-6 of the electronics module of FIG. 5 where the case housing includes the thin layer adhered to the inner surface of the case housing;

FIG. 7 is a close-up cross-sectional view showing another version of the standalone electronics case housing to include sock-like inner enclosure to house the circuit board electronics in the case housing;

DESCRIPTION OF THE INVENTION

Certain exemplary embodiments will now be described to provide an overall understanding of the principles of the structure, function, manufacture, and use of the device and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present disclosure. Further, in the present disclosure, like-numbered components of the embodiments generally have similar features, and thus within a particular embodiment each feature of each likenumbered component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Further, to the extent that directional terms like proximal, distal, top, bottom, up, or down are used, they are not intended to limit the systems, devices, and methods disclosed herein. A person skilled in the art will recognize that these terms are merely relative to the system and device being discussed and are not universal.

In the prior art, it is well known to bundle common surgical instruments which are required for a particular type of surgical procedure together in specialized kits. There are numerous health and safety requirements for these kits including tight inventorying and sterilization. Current systems rely on manual recording of the particular kits by serial number, the number of uses of each kit, and the locations of such uses. However, current systems lack the ability to automatically track the location and uses of each kit, notify end users of that data, and continue to provide that data even during high temperature sterilization processes.

Figure 1:
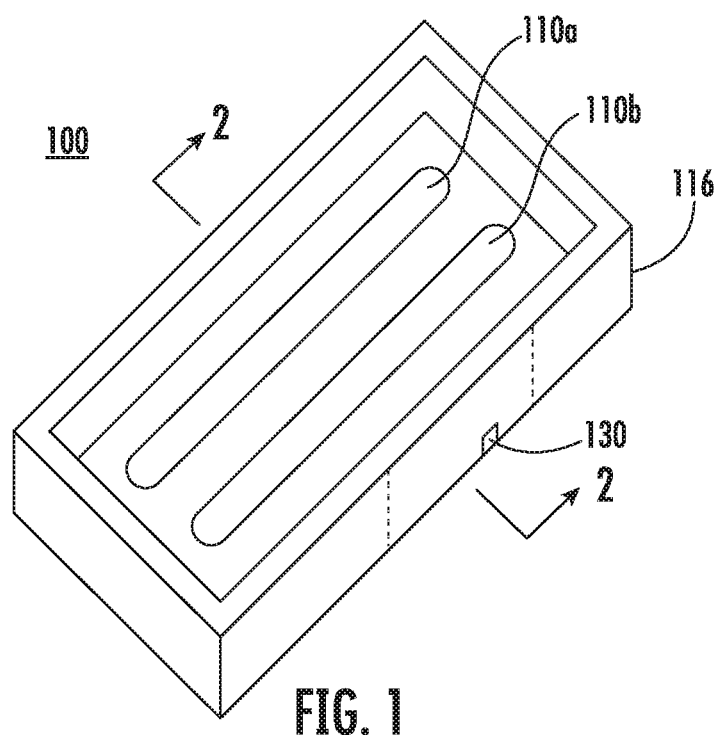
FIG. 1 is perspective view of a medical kit according to a first embodiment.
Figure 2:
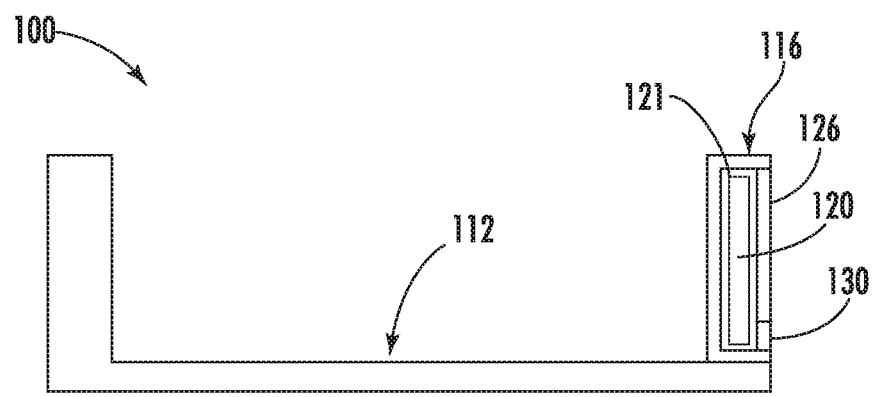
FIG. 2 is a sectional elevational view through the line 2-2 of the instrument kit tracking system of FIG. 1.

As shown in FIGS. 1 and 2, a first embodiment of a surgical kit 100 can include one or a plurality of medical instruments, or tools 110a, 110b. An example of such an instrument kit is 100 shown in FIG. 10. The kit 100 can be in the form of a tray 112, as representationally shown, or can be in the form of a bag or other types of containers. The tray 112 can be made of any material that is capable of being sterilized, including but not limited to stainless steel and other metals. The tray 112 can include tool supports or cavities to retain the tools 110a, 110b relative to one another to avoid any damage thereto. Moreover, as shown in FIG. 10, a tray 212 can include a cover 214 of any type to protect the tools 110a, 110b from the outside environment after sterilization in an autoclave, not shown.

Figure 10:
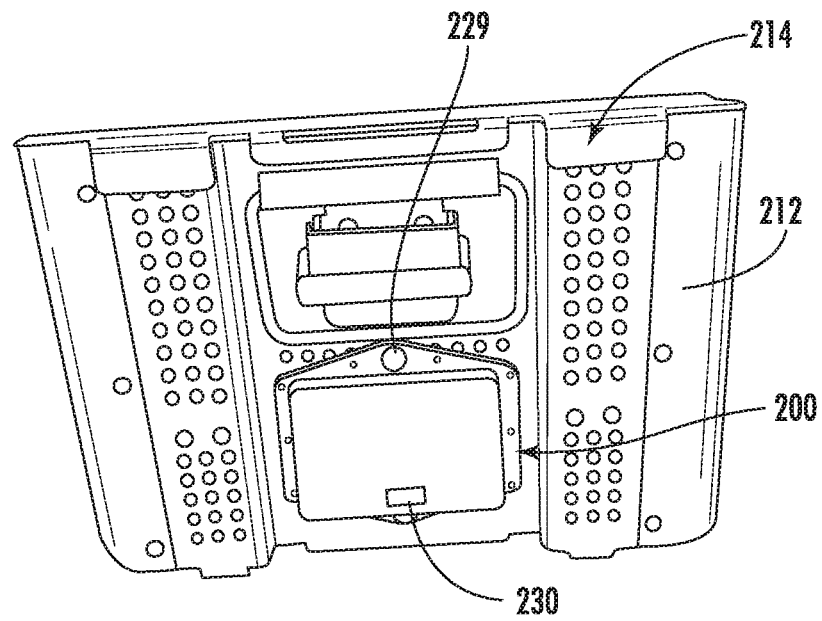
FIG. 10 is a side view of the standalone module of FIG. 5, containing the tracking electronics therein, affixed to the side of an instrument kit, such as by rivets.

An electronic tracking device 120 can be included on the kit 100, disposed in a side wall 116 of the tray, as shown in the embodiments of FIGS. 1-4, or on a side wall 216 of the tray 200 as shown in FIGS. 5 and 10. The tracking device 120 can be any number of tracking devices. For example, the tracking device 120 can include a power source 122 and a temperature sensor 124. The temperature sensor 124 can record temperature changes that are likely to occur in an autoclave during sterilization, as discussed below. The temperature sensor 124 is preferably solid state but can be any type of temperature sensor and one that can sense temperatures up to and beyond temperatures used for sterilization by known sterilization equipment.

While not shown, the tracking device can alternatively or additionally, include a processor; a memory: a one-way or two-way communications module, e.g. BLUETOOTH, cellular connections; and/or at least one type of location sensor including GPS, BLUETOOTH, WI-FI, Cellular Triangulation or other types of location sensors. Such communications components are so well known that they do not need to be shown or discussed further herein. Advantageously, such communication modules In some embodiments, the power source 122 can be sized to maintain functionality for five or more years and for more than 500 sterilization cycles. For example, the power source 122 can be any kind of battery, rechargeable or not. Advantageously, the electronic tracking device 120 can be permanently attached to either the inside or the outside of the tray (such as by rivets 229, adhesive, brackets or other fasteners as in FIG. 10) such that it cannot be removed intentionally or accidentally. In the illustrated embodiment, the electronic tracking device 120 can be disposed within a locked compartment 121 having a door 126 with a lock 130, such as seen in FIGS. 1-4. In an alternative embodiment, the compartment 121 can be similar to a drawer which can be withdrawn as a unit from the tray. The compartment can be locked by means of a mechanical lock 130 and key, an electronic locking mechanism, or a magnetic locking system, disposed on the door.

As noted above, the trays 112 and instruments 110a, 110b all need to be sterilized before and after use in a medical procedure. One such sterilization process, such as one that is carried out using an autoclave, subjects the tray 112, and thus the electronic tracking device 120, to being washed in an ultrasonic water bath solution and then steam sterilized at high temperatures around 120° C. to 135° C. in an autoclave. In some examples, the high temperatures can exceed 135° C.

Since the aforementioned electronics 126 typically operate in the range of up to 85° C., the present invention provides the necessary housing thereabout to protect the electronic during sterilization that far exceeds the operating temperature of the electronics. Moreover, the tray 112 of the instrument kit tracking system and method of the present invention can be designed to survive over 500 cycles of steam sterilization without destroying the electronic tracking device disposed therein. For example, the locked compartment 121 containing the electronic tracking device 120 can be designed to protect the tracking device from the aforementioned steam sterilization temperatures. As noted above, the tray/housing 112 can include a temperature sensor 124 can record such temperature changes and indicate a usage after the sensor has recorded a predefined high temperature setting that is associated with a sterilization through an autoclave. In some embodiments, the electronics 123, including the temperature sensor 125 and the power source 122 can be designed to withstand autoclave temperatures, discussed above, without any insulation such that they do not fail. The electronics 123 can include a memory to record these temperature changes as a usage and a processor to calculate the number of uses. Additionally, or alternatively, the electronics 123 can include a communications module to wirelessly communicate the temperature changes to an external CPU module, e.g. a smart phone, tablet, or a computer. In some embodiments, the communications modules can be programed such that they can automatically, without additional instructions, communicate the recorded temperature change, as a use, to as third-party device. In some embodiments, the recorded temperature change can additionally include location data which can be provided by the electronic 123, including GPS, BLUETOOTH, WI-FI, Cellular Triangulation or other types of location sensors. Advantageously, the instant tracking device 120 can provide real, or near real, time use and location data for the instrument tray without any additional interaction by users.

The electronic tracking device 120 can be defined by a compartment housing 140 that itself is preferably made of a polymer material but can be any suitable material. The housing 140 can be constructed to include a thin layer of material 142 that can be both hydrophobic and breathable in nature. For example, the hydrophobic layer may be epoxy, silicone, polyimide or silica aerogel. In some embodiments, the thin layer of material 142 can have a thickness of 6-10 mm but could be any thickness, such a thickness less than 6 mm, such as 1 mm, or greater than 10 mm. Moreover, the materials can be chosen to shield the electronics from the above noted autoclave temperatures. This layer of material 142 can work in conjunction with the actual polymer case 140 material type and can be designed to provide an air chamber around the electronics to provide an additional thermal barrier. This is one example of such a compartment, any compartment construction capable of permitting electronic signals to pass therethrough while protecting the internal electronics from autoclave temperatures is deemed to be within the scope of this disclosure.

Figure 3:
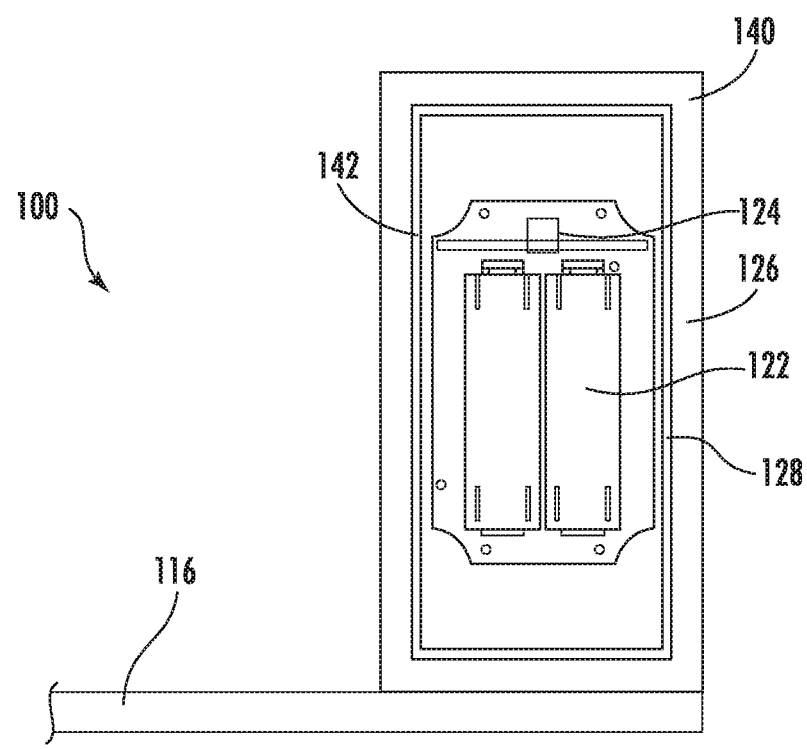
FIG. 3 is a close-up sectional view of the embodiment of the present invention that employs a thin layer of material adhered directly to the inner surface of the case housing that is embedded in the instrument kit.
Figure 4:
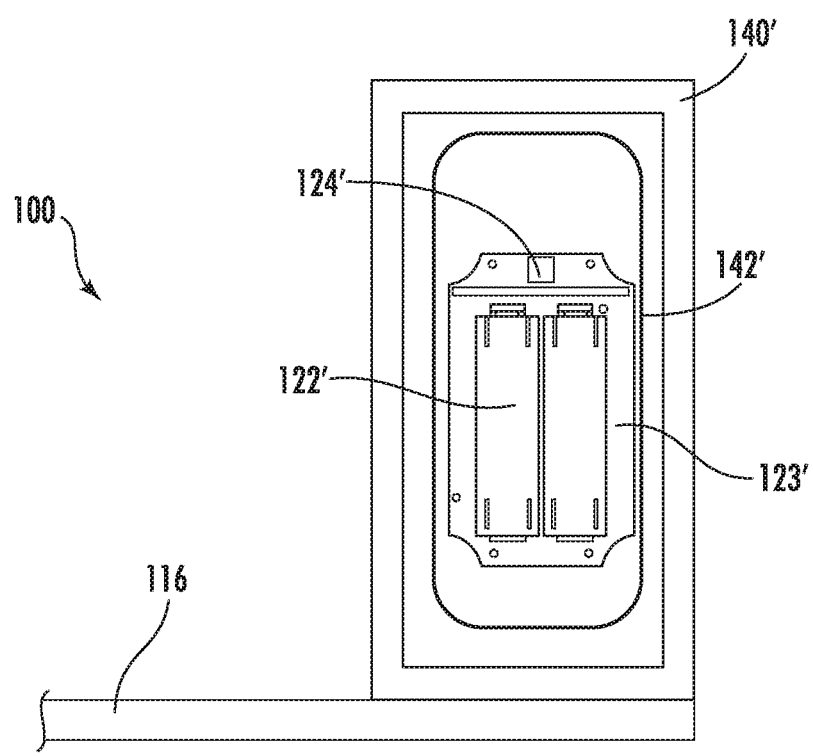
FIG. 4 is a close-up sectional view of the embodiment of the present invention employing a sock-like inner enclosure to house the circuit board electronics in the case housing.

Further, it is envisioned that the thin layer material 142 can be located on the inside of the polymer housing 140 and affixed thereto, such as by glue or adhesive to the polymer case surrounding the electronics, as in FIG. 3. Alternatively, as in FIG. 4, the thin layer 142' can be constructed as a sock or insert where the circuit board assembly 123' (including the power source 122' and at least a temperature sensor 124') is slipped into the sock then placed inside the polymer case housing 140'.

A standalone electronics module 200, that is affixed by rivets and the like, is shown in a second embodiment of FIGS. 5-7 and 10. In this second embodiment of the present invention, the location tracking electronics 223 are contained within a separate standalone electronics module 200 that is secured to an instrument kit 212/214, such as by rivets 229, or the like via mounting tabs on the case housing 240 of the module 200. Similar to the first embodiment, the standalone case housing 240 preferably includes an additional thin layer of material 242, which is preferably hydrophobic and also breathable. FIG. 6 shows a cross-sectional view through a version of the electronics module 200 of FIG. 5 where the case housing 240 inside includes the thin layer of material 242 adhered to the inner surface of the case housing 240. Alternatively, the thin layer 242 can be constructed as a sock or insert where the circuit board assembly 223' is slipped into the sock then placed inside the polymer case housing 240. Of note, the housing 240 and the thin layer of material 242 can be substantially similar to the materials described above with respect to the housing 140 and thin layer of material 142. FIG. 7, shows an alternative version of the standalone electronics case 200' housing that includes a sock-like inner enclosure 242' to surround the circuit board electronics 223' within the case housing 240'. The sock-like inner enclosure is preferably silica aerogel, glass fiber, or silicone fiber, but may be any other suitable material.

FIG. 10 shows a side view of the standalone case housing 200, containing the tracking electronics therein, affixed to the side of an instrument kit 214, preferably by the rivets 229. The housing 200 is preferably plastic or any other material, such as Polypropylene or polyphenylsulfone, that is suitable for withstanding high heat during an instrument sterilization process. Any other attachment fasteners can be employed and still be within the scope of the present invention. Adhesives and other fasteners may also be used to secure the electronics module 200 to the side 212 of the instrument kit 214. It is also preferred that the tracking device 200, including its electronics 223', be controllably affixed to the instrument kit 214 for tamper proof and security purposes. For example, a special latching mechanism, or lock, 230 may be employed for this purpose to attach and detach the tracking device from the instrument kit with a special key. For example, the electronics case module 200 can be attached by rivets or other mechanism such adhesive or other types of fasteners. The electronics module 200 can be attached using a releasable security lock 230 where the electronics module can be attached and detached from the instrument kit 214 but only by use of the special key. In the embodiment of FIGS. 1-4, the access door 126 could be secured by a lock 130 with a special key.

Figure 8A:
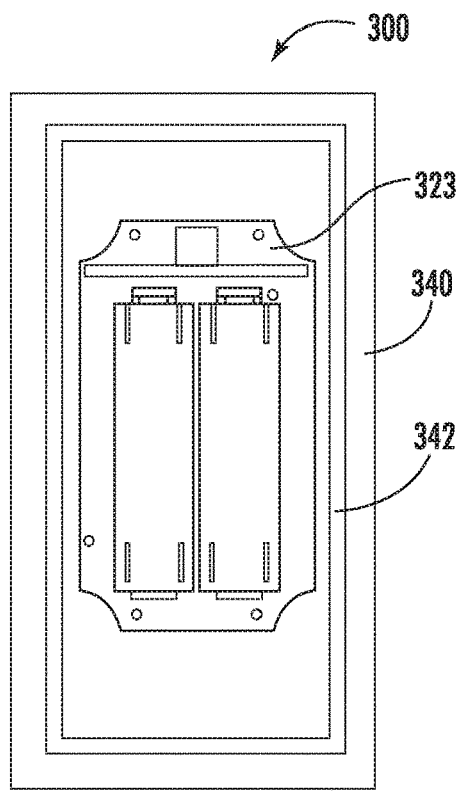
FIGS. 8A and 8B show additional embodiments of the standalone electronics module where the circuit board is vacuum sealed.
Figure 8B:
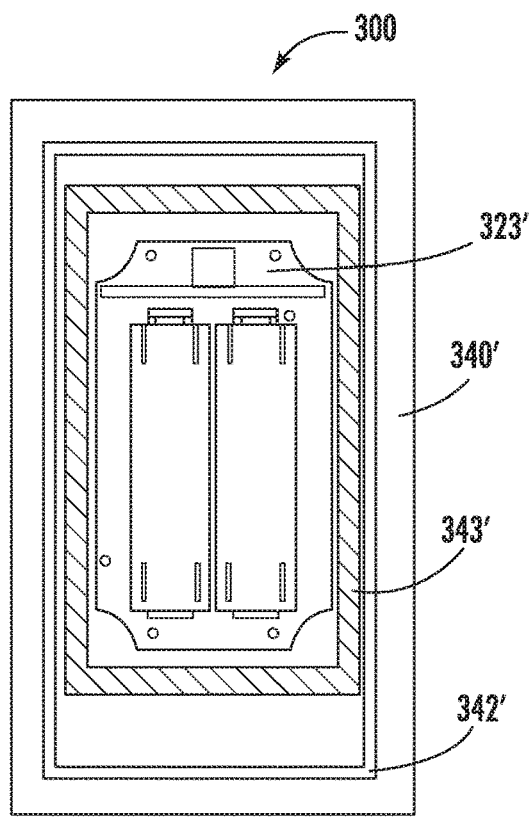

In a third alternative embodiment of the present invention of FIGS. 8A and 8B, in place of the thin layer of material 142, 242 affixed to an inner surface of the respective housings, or the sock like thin layer of material 142', 242' disposed around the respective electronics, a layer of material 342 is vacuum sealed around the electronics 323, as shown in FIG. 8A. FIG. 8B, shows a cross-sectional view showing another version of the standalone electronics case housing 340' that includes an inner liner 343' to surround the circuit board electronics 323' within the vacuum sealed material 342' in the case housing. Any combination of the foregoing layers and liners may be used and still be within the scope of the present invention.

Figure 9:
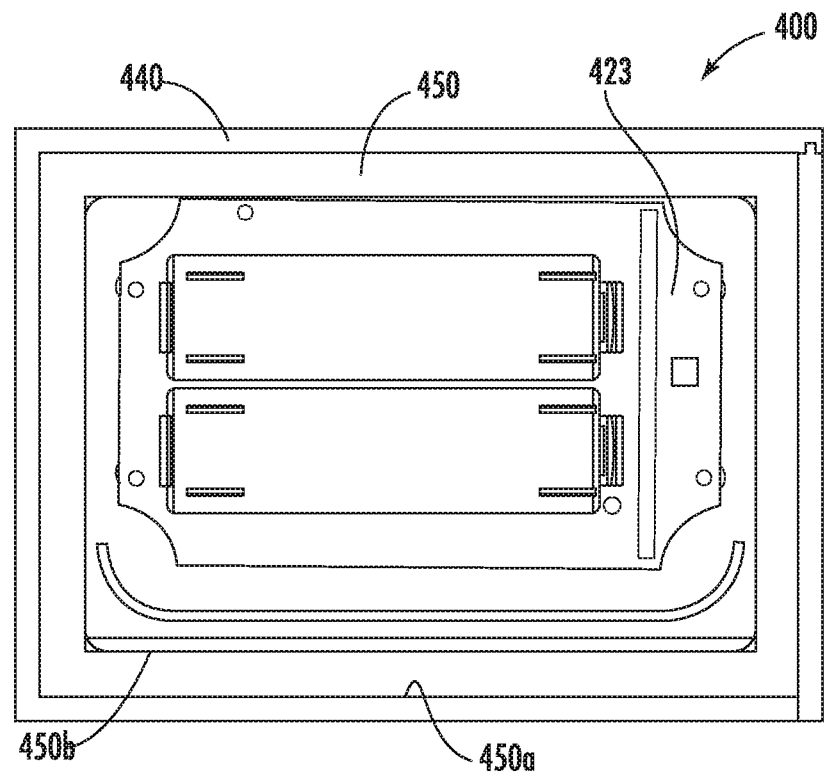
FIG. 9 is showing yet another embodiment of an electronics module that includes a layer of insulation.

FIG. 9 illustrates a further alternative embodiment 400 of the present invention that includes an additional feature that provides a layer of insulation 450 between the housing 440 and the circuit board electronics 423. The insulation 450 is preferably silica aerogel but may be any suitable material depending on the application at hand. It is understood that the insulation 450 of FIG. 9 can be used in any of the above configurations without departing from the scope of the embodiments, including an inner layer of the thin material 142 in FIG. 3, the sock like embodiment 142' of FIG. 4, or the vacuum sealed version 342 of FIG. 8A. In the case where the circuit board electronics 423 includes a temperature sensor 224 as seen in FIG. 6, for example, the high temperatures recorded during an autoclave disinfecting wash may be lower than those recorded in a sensor 224 without the insulation 450. A thin layer of the same material as the thin layer 142 can be use on an outer 450a or inner 450b surface of the insulation, or both. The inner layer 142 may or may not be used depending on the application at hand.

The instrument kit tracking system and methods of the present invention provide the ability to periodically monitor and report, such as on a daily basis, but could be any pre-defined or on-demand reporting cycle such as hourly, weekly, or monthly. The reports can detail, in some embodiments, the exact location of each kit. Moreover, the instrument kit tracking system and method of the present invention can record and transmit, within the same daily schedule, all date stamps, locations, and number of surgeries the kit has been involved in. A cloud-based system can be included to capture data on a daily basis and report out to the user or manager the particular status of each deployed kit. The cloud-based system can additionally alert end users of any kit that may have reached a predefined limitation on the number of surgeries performed so that the kit can be returned, and instruments replaced or calibrated before going back out for deployment.

In the present embodiments the number of surgeries can recorded and tracked in many different ways. For example, the invention can record and track the surgeries by tracking the temperature of the device using a built-in temperature sensor. The cycling of temperature from a low, or nominal, temperature to a high temperature can be parsed, or understood, to represent a disinfecting wash cycle and a separate autoclave cycle, which is helpful in better understanding the compliance and usage information of the device and the instruments therein. For example, the average low temperature can be representative of transport to and usage during a surgical procedure. Other tracking methodologies could be used, such as pressure or an accelerometer, and any other methodologies that can carry out recording the number of surgeries. The instrument kit tracking system and method of the present invention offers greater efficiency in inventory management, deployment, accountability of the assets, automatic annual inventory auditing, complete compliance to instrument usage and documentation, and ease of inventory recovery during product recalls.

It will be appreciated by those skilled in the art that various changes and modifications can be made to the illustrated embodiments without departing from the spirit of the present disclosure. All such modifications and changes are intended to be covered by the appended claims.

What is claimed is:

1. A tracking system for a medical instrument kit, comprising:
 a housing; and
 an electronics module contained within the housing, wherein the tracking system is configured and arranged to withstand external temperatures between 120-135° C.;
 wherein the tracking system is configured and arranged to be affixed to the medical instrument kit, the medical instrument kit is configured and arranged to receive at least one medical instrument;
 wherein the electronics module includes a power source, a location sensor, and a temperature sensor; wherein the temperature sensor is configured and arranged to record a temperature reading and calculate a usage of the at least one medical instrument if the temperature reading is above a predetermined value; and
 wherein, the internal temperature of the electronics module is maintained such that an electronic device contained therein is operable when the external temperature is between 120-135° C.

2. The tracking system of claim 1,
 wherein the tracking system is a standalone unit with the electronics module with electronics residing in the housing; and
 wherein the housing is affixed to an outer wall of the medical instrument kit.

3. The tracking system of claim 1, wherein the tracking system is embedded in a wall of the medical instrument kit.

4. The tracking system of claim 1,
 wherein the tracking system is a standalone unit with the electronics module having electronics residing in the housing;
 wherein the housing is contained inside a medical instrument kit.

5. The tracking system of claim 1, further comprising:
 a layer of material disposed between the electronics module and an outer wall of the housing; the layer of material being hydrophobic breathable.

6. The tracking system of claim 5, wherein the layer of material is adhered to an inner wall of the housing.

7. The tracking system of claim 5, wherein the layer of material is configured as a sock-like member configured for containing electronics therein.

8. The tracking system of claim 5, wherein the layer of material has a thickness of 1 mm.

9. The tracking system of claim 5, wherein the layer of material has a thickness of 6-10 mm.

10. The tracking system of claim 1, wherein access to the electronics is selectively lockable.

11. The tracking system of claim 1, wherein the predetermined value is representative of an autoclave cycle.

12. The tracking system of claim 1, wherein the electronics module further includes a communications module for communicating operational parameters of the medical instrument kit.

13. The tracking system of claim 12, wherein the operational parameters are a temperature reading, usage of the medical instrument kit, and location of the medical instrument kit.

* * * * *